US011045760B2

(12) United States Patent
Chareyre et al.

(10) Patent No.: US 11,045,760 B2
(45) Date of Patent: Jun. 29, 2021

(54) MEMBRANE PERMEATION TREATMENT WITH ADJUSTMENT OF THE TEMPERATURE OF THE FIRST RETENTATE AS A FUNCTION OF THE CH4 CONCENTRATION IN THE THIRD AND/OR FOURTH PERMEATE

(71) Applicant: L'Air Liquide, Societe Anonyme pour l'Etude et l'Exploitation des Procedes Georges Claude, Paris (FR)

(72) Inventors: Jean-Marc Chareyre, Voiron (FR); Veronique Grabie, Coublevie (FR); Golo Zick, Fontaine (FR)

(73) Assignee: L'Air Liquide Societe Anonyme Pour L'Etude Et L'Exploitation Des Procedes Georges Claude, Paris (FR)

( * ) Notice: Subject to any disclaimer, the term of this patent is extended or adjusted under 35 U.S.C. 154(b) by 0 days.

(21) Appl. No.: 16/536,299

(22) Filed: Aug. 8, 2019

(65) Prior Publication Data
US 2020/0047112 A1 Feb. 13, 2020

(30) Foreign Application Priority Data
Aug. 8, 2018 (FR) ...................................... 1857383

(51) Int. Cl.
*B01D 53/22* (2006.01)
*B01D 53/30* (2006.01)
(Continued)

(52) U.S. Cl.
CPC ........... *B01D 53/226* (2013.01); *B01D 53/30* (2013.01); *C07C 7/005* (2013.01); *C07C 7/144* (2013.01); *B01D 2053/221* (2013.01)

(58) Field of Classification Search
CPC .. B01D 53/225; B01D 53/226; B01D 53/228; B01D 53/30; B01D 2053/221;
(Continued)

(56) References Cited

U.S. PATENT DOCUMENTS 5,670,051 A * 9/1997 Pinnau ................ B01D 53/228
210/500.27
8,999,038 B2 4/2015 Ungerank et al.
(Continued)

FOREIGN PATENT DOCUMENTS

EP 2 735 355 5/2014
FR 3 025 117 3/2016

OTHER PUBLICATIONS

Search Report and Written Opinion for FR 1857383, dated May 23, 2019.

*Primary Examiner* — Youngsul Jeong
*Assistant Examiner* — Jason Y Chong
(74) *Attorney, Agent, or Firm* — Christopher J. Cronin

(57) ABSTRACT

A facility and method for membrane permeation treatment of a feed gas flow containing at least methane and carbon dioxide that includes a compressor, a pressure measurement device, at least one valve, and first, second, third, and fourth membrane separation units for separation of $CO_2$ from $CH_4$ to permeates enriched in $CO_2$ and retentates enriched in $CH_4$, respectively. A temperature of the first retentate is adjusted at an inlet of the second membrane separation unit with at least one heat exchanger as a function of the measured $CH_4$ concentration in such a way so as to reduce the determined difference.

5 Claims, 2 Drawing Sheets

(51) Int. Cl.
*C07C 7/00* (2006.01)
*C07C 7/144* (2006.01)

(58) Field of Classification Search
CPC ........ B01D 2256/245; B01D 2257/504; B01D 2258/05; C07C 7/005; C07C 7/144; Y02C 20/40; C10L 2290/06; C10L 2290/12; C10L 2290/26; C10L 2290/46; C10L 2290/548; C10L 2290/58; C10L 2290/60; C10L 3/104
See application file for complete search history.

(56) References Cited

U.S. PATENT DOCUMENTS

| | | |
|---|---|---|
| 2012/0000355 A1 | 1/2012 | Sharma et al. |
| 2015/0336046 A1 | 11/2015 | Ungerank et al. |
| 2016/0229771 A1* | 8/2016 | Paget .................... B01D 53/226 |
| 2017/0304769 A1* | 10/2017 | Bigeard ................... F25J 3/08 |

* cited by examiner

MEMBRANE PERMEATION TREATMENT WITH ADJUSTMENT OF THE TEMPERATURE OF THE FIRST RETENTATE AS A FUNCTION OF THE CH4 CONCENTRATION IN THE THIRD AND/OR FOURTH PERMEATE

CROSS-REFERENCE TO RELATED APPLICATIONS

This application claims the benefit of priority under 35 U.S.C. § 119 (a) and (b) to French patent application No. FR 1857383, filed Aug. 8, 2018, the entire contents of which are incorporated herein by reference.

BACKGROUND

Field of the Invention

The present invention relates to a facility for the treatment by membrane permeation of a gas stream containing at least methane and carbon dioxide in order to produce a methane-rich gas stream, of which the methane content meets the requirements of its use and to a method for controlling such a facility.

It relates in particular to the purification of biogas, with the aim of producing biomethane in accordance with the specifications for injection into a natural gas network.

Related Art

Biogas is the gas produced as organic matter breaks down in the absence of oxygen (anaerobic fermentation), also referred to as methanization. This may be natural breakdown—it is thus found in marshland or in discharges from household waste—but the production of biogas may also result from the methanization of waste in a dedicated reactor referred to as a methanizer or digester.

Because of its chief constituents—methane and carbon dioxide—biogas is a powerful greenhouse gas; at the same time, it also constitutes a source of renewable energy that is appreciable in the context of the increasing scarcity of fossil fuels.

Biogas contains mainly methane ($CH_4$) and carbon dioxide ($CO_2$) in proportions that can vary according to the way in which it is obtained, but also contains, in smaller proportions, water, nitrogen, hydrogen sulfide, oxygen and other organic compounds, in trace form.

Depending on the organic matter that has been broken down and on the techniques used, the proportions of the components differ, although on average biogas contains, in the dry gas, from 30 to 75% methane, from 15 to 60% $CO_2$, from 0 to 15% nitrogen, from 0 to 5% oxygen and trace compounds.

Biogas is put to profitable use in various ways. It may, after light treatment, be put to profitable use near the production site in order to supply heat, electricity or a mixture of both (cogeneration); the high carbon dioxide content reduces its calorific value, increases the cost of compression and transport and limits the economic benefit of putting it to profitable use in this way nearby.

Purifying the biogas to a greater degree allows it to be put to broader use, in particular, extensive purification of the biogas yields a biogas that has been purified to the specifications of natural gas and which can be substituted for the latter; biogas thus purified is known as "biomethane". Biomethane thus supplements the natural gas resources with a renewable proportion produced within the territories; it can be put to exactly the same uses as natural gas of fossil origin. It can be fed into a natural gas network, a vehicle filling station; it can also be liquefied to be stored in the form of liquefied natural gas (LNG) etc.

The ways in which the biomethane is put to profitable use are determined according to the local context: local energy requirements, possibilities for putting it profitable use as a biomethane fuel, and whether there is a natural gas transport or distribution network nearby, in particular. By creating synergy between the various parties operating in a given territory (agriculture, industry, civic authorities), the production of biomethane assists the territories in acquiring greater self-sufficiency in terms of energy.

There are a number of steps that need to be gone through between collecting the biogas and obtaining the biomethane, the end-product that can be compressed or liquefied.

In particular, there are several steps needed prior to treatment which is aimed at separating the carbon dioxide in order to produce a stream of purified methane. A first step is to compress the biogas which has been produced and brought in at atmospheric pressure, and this compression can be obtained—in the conventional way—using a compressor. The next steps are aimed at ridding the biogas of its corrosive components which are hydrogen sulfide and the volatile organic compounds (VOCs), the technologies used for this are, in the conventional way, pressure swing adsorption (PSA) and activated carbon capture. Next comes the step which consists in separating the carbon dioxide in order ultimately to obtain methane at the purity required for its subsequent use.

Carbon dioxide is a contaminant typically present in natural gas and it is common practice to need to remove it. Varying technologies are used for this depending on the situation; among these, membrane technology performs particularly well when the $CO_2$ content is high; and it is therefore used for separating the $CO_2$ present in biogas and in particular in landfill gas.

Membrane gas-separation methods used for purifying a gas, whether they employ one or more membrane stages, need to be able to produce a gas at the required quality, at a low cost, while at the same time minimizing the losses of the gas that is to be put to profitable use. Thus, in the case of biogas purification, the separation performed is chiefly a $CH_4/CO_2$ separation which needs to allow the production of a gas containing, depending on its use, more than 85% $CH_4$, preferably more than 95% $CO_2$, more preferentially more than 97.5% $CH_4$, while minimizing the $CH_4$ losses in the residual gas and the cost of purification, the latter to a large extent being associated with the electricity consumption of the device that compresses the gas upstream of the membranes.

It is preferable for the facilities that allow the production of a methane-enriched gas flow to be able to control the methane loss.

From that point on, a problem which arises is that of providing a facility which makes it possible to obtain a methane stream at constant concentration such that the equipment that uses the biomethane has a consistent operation.

SUMMARY OF THE INVENTION

One solution of the present invention is a facility for the membrane permeation treatment of a feed gas flow containing at least methane and carbon dioxide, comprising:

a compressor for compressing the feed gas flow, a first membrane separation unit able to receive the gas flow coming from the compressor and to supply a first permeate and a first retentate, a second membrane separation unit able to receive the first retentate and to supply a second permeate and a second retentate, a third membrane separation unit able to receive the first permeate and to supply a third permeate and a third retentate, a fourth membrane separation unit able to receive the third retentate and to supply a fourth permeate and a fourth retentate, at least a first means for measuring the $CH_4$ concentration in the third permeate or the fourth permeate or in a flow combining the third permeate or the fourth permeate, and at least one means for adjusting the temperature of the first retentate at the inlet of the second membrane separation unit as a function of the measurement recorded by the first measuring means;

with each membrane separation unit comprising at least one membrane that is more permeable to carbon dioxide than to methane.

DETAILED DESCRIPTION OF THE INVENTION

Figure 1:
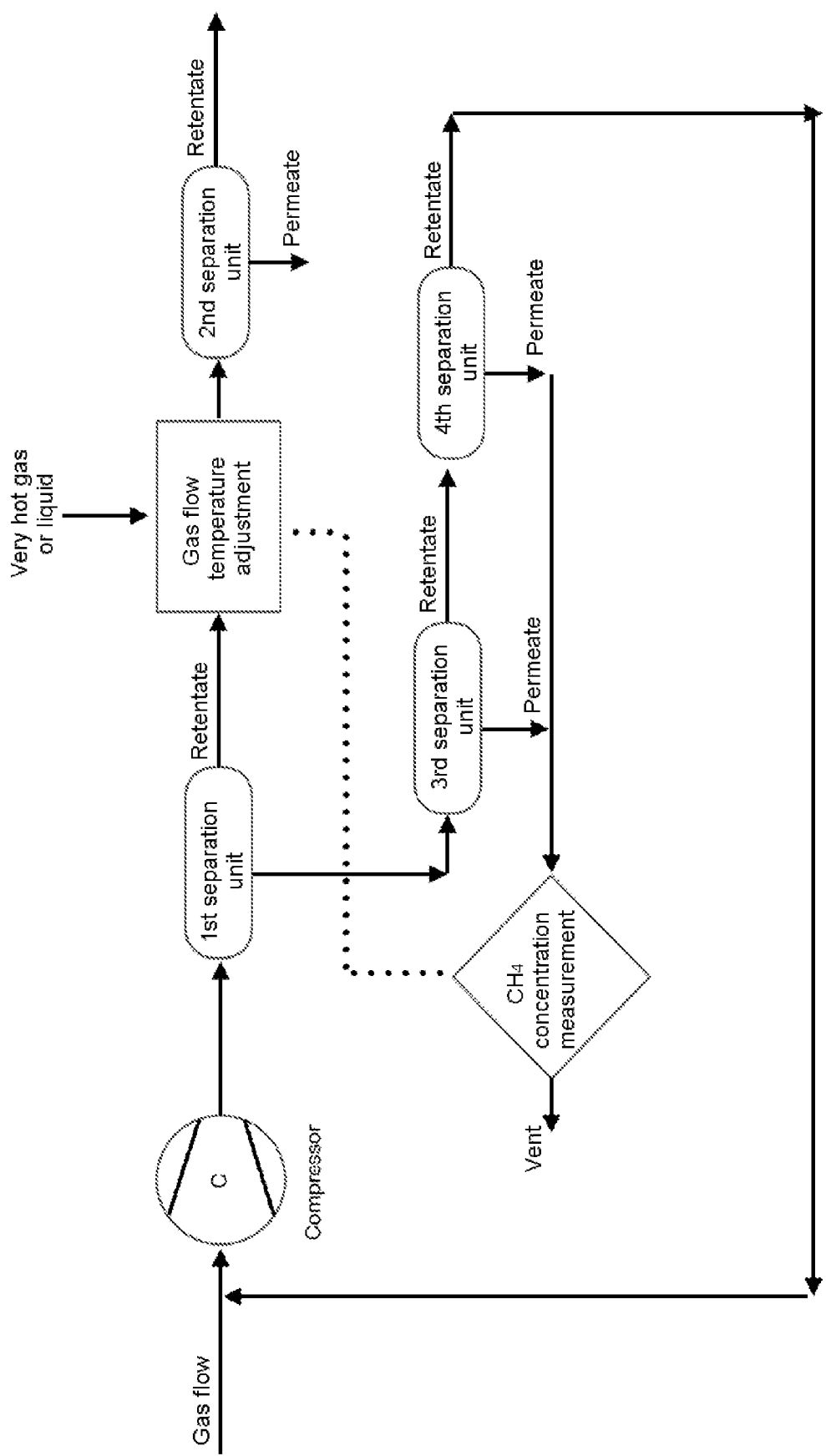
FIG. 1 is a schematic of an example of the multi-stage separation of the invention.

Depending on the case, the facility according to the invention may have one or more of the following features:

the first measuring means is carried out by a gas analyzer;

the adjusting means is a heat exchanger using a secondary flow having a temperature higher or lower than the temperature of the first retentate. It should be noted that this secondary flow may be liquid or gas. Its temperature will preferably be higher and will preferably be between 1.2 times the temperature of the first retentate and 100 times the temperature of the first retentate, more preferentially between 2 times the temperature of the first retentate and 80 times the temperature of the first retentate, even more preferentially between 2.5 times the temperature of the first retentate and 50 times the temperature of the first retentate;

FIG. 1 illustrates an example of a facility according to the invention with a secondary flow having a temperature higher than the temperature of the first retentate;

the fourth retentate is recycled to the compressor for compressing the feed gas flow.

the membranes used in the membrane separation units have the same selectivity.

at least one membrane separation unit comprises at least two membranes with the same selectivity.

at least one membrane separation unit comprises at least two membranes with different selectivities.

at least one membrane separation unit uses a membrane with a selectivity different from the selectivity of the membranes of the other membrane separation units.

A subject of the present invention is also a method for controlling a facility as defined in the invention, comprising the following steps:

a step of measuring the $CH_4$ concentration in the third permeate or the fourth permeate or in a flow combining the third permeate or the fourth permeate. The measurement will preferably be carried out by a gas analyzer;

a step of comparing this measurement with a setpoint value, and of determining the difference with respect to this setpoint value, and a step of adjusting the temperature of the first retentate at the inlet of the second membrane separation unit such a way as to reduce the determined difference.

Figure 2:
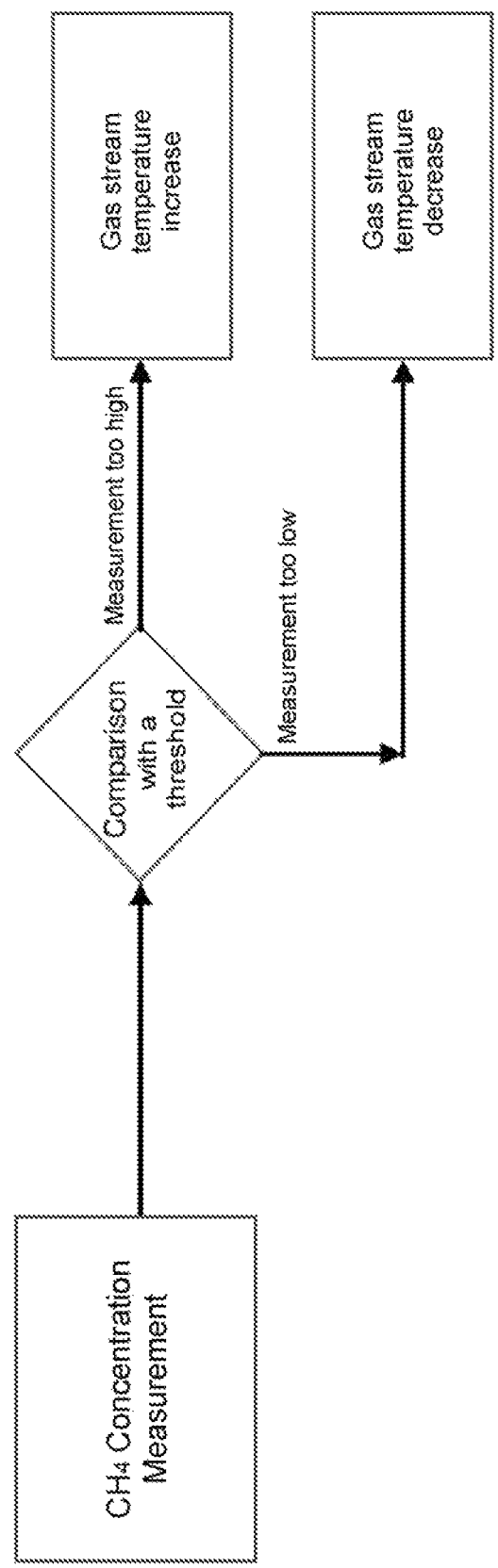
FIG. 2 is a process flow chart illustrating an aspect of the invention.

FIG. 2 illustrates the method according to the invention.

As appropriate, the method according to the invention can exhibit one or more of the features below:

the adjusting of the temperature of the first retentate is carried out by heat exchange between a secondary flow having a temperature higher or lower than the temperature of the first retentate. The heat exchange is carried out within the heat exchanger of the facility according to the invention;

the adjusting step comprises an increase or a decrease in the temperature;

the feed gas flow is biogas;

the comparing step and the adjusting step are carried out automatically by data transmission and data processing means. A data transmission and data processing means may for example be an industrial processor of the programmable controller type.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing i.e. anything else may be additionally included and remain within the scope of "comprising." "Comprising" is defined herein as necessarily encompassing the more limited transitional terms "consisting essentially of" and "consisting of"; "comprising" may therefore be replaced by "consisting essentially of" or "consisting of" and remain within the expressly defined scope of "comprising".

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

What is claimed is:

1. A method for membrane permeation treatment of a feed gas flow containing at least methane and carbon dioxide, comprising:

compressing the feed gas flow with a compressor;

receiving a flow of gas coming from the compressor at a first membrane separation unit that supplies a first permeate and a first retentate;

receiving the first retentate at a second membrane separation unit that supplies a second permeate and a second retentate;

receiving the first permeate at a third membrane separation unit that supplies a third permeate and a third retentate;

receiving the third retentate at a fourth membrane separation unit that supplies a fourth permeate and a fourth retentate;

with a gas analyzer, measuring a $CH_4$ concentration of the third permeate, a $CH_4$ concentration of the fourth permeate, or a $CH_4$ concentration of a flow of gas that is comprised of a combination of the third permeate and the fourth permeate;

comparing the measured $CH_4$ concentration with a setpoint $CH_4$ concentration and determining a difference therebetween; and adjusting a temperature of the first retentate at an inlet of the second membrane separation unit with at least one heat exchanger as a function of the measured $CH_4$ concentration in such a way so as to reduce the determined difference, wherein each membrane separation unit comprises at least one membrane that is more permeable to carbon dioxide than to methane.

2. The method of claim 1, wherein the adjusting of the temperature of the first retentate is carried out by heat exchange with a secondary flow having a temperature higher or lower than the temperature of the first retentate.

3. The method of claim 1, wherein the adjusting step comprises increasing or decreasing the temperature of the first retentate.

4. The method of claim 1, wherein the feed gas flow is biogas.

5. The method of claim 1, wherein said steps of comparing, determining, and adjusting step are carried out automatically by a programmable controller.

* * * * *